(12) United States Patent  
Coldren et al.

(10) Patent No.: US 9,301,874 B2  
(45) Date of Patent: Apr. 5, 2016

(54) PUNCTAL PLUGS FOR CONTROLLED RELEASE OF THERAPEUTIC AGENTS

(75) Inventors: Bret A. Coldren, Vista, CA (US); Peter Paul Willem Leonard Van Den Bekerom, Nuenen (NL); Antonius Wilhelmus Maria De Laat, Den Dungen (NL); Johannes Wilhelmus Weekamp, Beek en Donk (NL); Victor Lust, Jacksonville, FL (US); Gerald Yewey, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 917 days.

(21) Appl. No.: 13/409,210

(22) Filed: Mar. 1, 2012

(65) Prior Publication Data  
US 2012/0283669 A1 Nov. 8, 2012

Related U.S. Application Data

(60) Provisional application No. 61/483,157, filed on May 6, 2011.

(51) Int. Cl.  
*A61F 9/00* (2006.01)  
*A61M 31/00* (2006.01)  
*A61F 9/007* (2006.01)  
*A61M 35/00* (2006.01)

(52) U.S. Cl.  
CPC ..... *A61F 9/00772* (2013.01); *A61F 2250/0068* (2013.01)

(58) Field of Classification Search  
CPC . A61F 9/0026; A61F 9/00772; A61F 9/0017; A61F 9/0008; A61M 31/00; A61K 9/0051; A61K 9/0019; A61K 9/0021

USPC ............ 604/294, 298, 890.1, 891.1, 892.1, 8; 600/300; 424/426–428  
See application file for complete search history.

(56) References Cited

U.S. PATENT DOCUMENTS

| | | |
|---|---|---|
| 3,618,604 A | 11/1971 | Ness |
| 3,626,940 A | 12/1971 | Zaffaroni |
| 3,826,258 A | 7/1974 | Abraham |
| 3,845,770 A | 11/1974 | Theeuwes et al. |
| 3,962,414 A | 6/1976 | Michaels |
| 3,993,071 A | 11/1976 | Higuchi et al. |
| 4,014,335 A | 3/1977 | Arnold |
| 4,923,699 A | 5/1990 | Kaufman |
| 5,017,381 A * | 5/1991 | Maruyama et al. ........... 424/472 |
| 5,962,548 A | 10/1999 | Vanderlaan et al. |

(Continued)

FOREIGN PATENT DOCUMENTS

WO WO 99/65544 A1 12/1999

OTHER PUBLICATIONS

International Search Report for corresponding Application No. PCT/US2012/035516 mailed Jul. 11, 2012.

*Primary Examiner* — Tan-Uyen (Jackie) T Ho  
*Assistant Examiner* — Mark Wardas  
(74) *Attorney, Agent, or Firm* — Carl J. Evens

(57) ABSTRACT

Lacrimal inserts such as punctal plugs may be utilized for delivery of medication to the eye. The plug includes a body portion sized to pass through a lacrimal punctum and be positioned within a lacrimal canaliculus of the eyelid. The plug may contain a core, or reservoir, at least partially within the body portion comprising a therapeutic agent that is configured for controlled, pulsatile release into the eye.

1 Claim, 7 Drawing Sheets

(56) References Cited

U.S. PATENT DOCUMENTS

| | | | |
|---|---|---|---|
| 6,020,445 | A | 2/2000 | Vanderlaan et al. |
| 6,099,852 | A | 8/2000 | Jen |
| 6,196,993 | B1 | 3/2001 | Cohan et al. |
| 6,367,929 | B1 | 4/2002 | Maiden et al. |
| 6,822,016 | B2 | 11/2004 | McCabe et al. |
| 2005/0197614 | A1* | 9/2005 | Pritchard et al. .................. 604/8 |
| 2008/0177153 | A1* | 7/2008 | Bachman et al. ............. 600/300 |
| 2009/0306608 | A1 | 12/2009 | Li et al. |
| 2011/0054418 | A1* | 3/2011 | Pugh et al. .................... 604/285 |
| 2011/0251568 | A1 | 10/2011 | Beeley et al. |

\* cited by examiner

PUNCTAL PLUGS FOR CONTROLLED RELEASE OF THERAPEUTIC AGENTS

CROSS REFERENCE TO RELATED APPLICATIONS

This patent application claims the benefit of U.S. Provisional Patent Application Ser. No. 61/483,157 filed May 6, 2011.

BACKGROUND OF THE INVENTION

1. Field of the Invention

The present invention relates to an ophthalmic insert and method for the release of medication to the eye for the treatment of eye disorders. More specifically, the present invention relates to punctal plugs sized to pass through a lacrimal punctum and be positioned within a lacrimal canaliculus of the eyelid and containing medication for autonomous and controlled release into the eye.

2. Discussion of the Related Art

Active agents frequently are administered to the eye for the treatment of ocular diseases and disorders. Conventional means for delivering active agents to the eye involve topical application to the surface of the eye. The eye is uniquely suited to topical administration because, when properly constituted, topically applied active agents may penetrate through the cornea and rise to therapeutic concentration levels inside the eye. Active agents for ocular diseases and disorders may be administered orally or by injection, but such administration routes are disadvantageous in that, in oral administration, the active agent may reach the eye in too low a concentration to have the desired pharmacological effect and their use is complicated by significant, systemic side effects and injections pose the risk of infection.

The majority of ocular active agents are currently delivered topically using eye drops which, though effective for some applications, are inefficient. When a drop of liquid is added to the eye, it overfills the conjunctival sac, the pocket between the eye and the lids, causing a substantial portion of the drop to be lost due to overflow of the lid margin onto the cheek. In addition, a substantial portion of the drop that remains on the ocular surface is drained into the lacrimal puncta, diluting the concentration of the drug.

To compound the problems described above, patients often do not use their eye drops as prescribed. Often, this poor compliance is due to an initial stinging or burning sensation caused by the eye drop. Certainly, instilling eye drops in one's own eye may be difficult, in part because of the normal reflex to protect the eye. Therefore, sometimes one or more drops miss the eye. Older patients may have additional problems instilling drops due to arthritis, unsteadiness, and decreased vision, and pediatric and psychiatric patient populations pose difficulties as well.

It is known to use devices that may be inserted into one or more of an orifice of an individual's eye, such as a lacrimal punctum, to deliver active agents. One disadvantage of using such devices to deliver agents is that much of the agent may delivered in an initial, large bolus upon insertion of the device into the eye rather than a more linear delivery of the agent over time.

Prior topical sustained release systems include gradual release formulations, either in solution or ointment form, which are applied to the eye in the same manner as eye drops but less frequently. Such formulations are disclosed, for example, in U.S. Pat. No. 3,826,258 issued to Abraham and U.S. Pat. No. 4,923,699 issued to Kaufman. Due to their method of application, however, these formulations result in many of the same problems detailed above for conventional eye drops. In the case of ointment preparations, additional problems are encountered such as a blurring effect on vision and the discomfort of the sticky sensation caused by the thick ointment base.

Alternatively, sustained release systems have been configured to be placed into the conjunctival cul-de-sac, between the lower lid and the eye. Such units typically contain a core drug-containing reservoir surrounded by a hydrophobic copolymer membrane which controls the diffusion of the drug. Examples of such devices are disclosed in U.S. Pat. No. 3,618,604 issued to Ness, U.S. Pat. No. 3,626,940 issued to Zaffaroni, U.S. Pat. No. 3,845,770 issued to Theeuwes et al., U.S. Pat. No. 3,962,414 issued to Michaels, U.S. Pat. No. 3,993,071 issued to Higuchi et al., and U.S. Pat. No. 4,014,335 issued to Arnold. However, due to their positioning, the units are uncomfortable and poor patient acceptance is again encountered.

Accordingly, there exists a need for a comfortable, implantable device, positionable within the lacrimal canaliculus of the eye to provide autonomous and controlled drug release.

SUMMARY OF THE INVENTION

The punctual plugs of the present invention overcome the limitations associated with the prior art as briefly described above.

In accordance with a first aspect, the present invention is directed to a lacrimal insert. The lacrimal insert comprising a body having a first end and a second end, a surface extending between the two ends, a cavity within the body, and a drug core insert, configured for insertion into the cavity of the lacrimal insert, wherein the drug core insert comprises a swell plate and a drug chamber; the swell plate comprising a timer channel and a plurality of swell chambers; the drug chamber comprising a drug channel in fluid communication with a fluid outlet and a plurality of discrete, active-agent containing, self-contained doses of therapeutic agent in fluid communication with the drug channel.

In accordance with another aspect, the present invention is directed to a drug core insert for a punctal plug. The drug core insert comprising a swell plate having a single or multiple timer channel, a plurality of swell chambers in fluid communication with the timer channels via a plurality of fluid ports connecting the swell chambers and the timer channels; and a fluid inlet port to permit fluid communication between the timer channels and the exterior of the swell plate, a drug plate comprising a plurality of discrete drug compartments, a single or multiple drug channel in fluid communication with the plurality of discrete drug compartments, and a fluid channels in fluid communication with each of the plurality of discrete drug compartments and the exterior of the drug plate, and a flexible membrane separating the drug plate and the swell plate, wherein the swell chambers and the plurality of discrete drug compartments are aligned to permit interaction between the swell chambers and the discrete drug compartments.

The punctal plugs of the present invention are sized to pass through a lacrimal punctum and be positioned within a lacrimal canaliculus of the eye and contain drugs(s) and/or therapeutic agent(s) for autonomous and controlled release into the eye. The punctal plugs comprise a cavity in which a drug delivery engine utilized fluid from the eye to drive a drug and/or combination of drugs or therapeutic agents contained in the drug delivery engine into the eye. The punctal plugs and the drug delivery engines are relatively simple and inexpensive to manufacture.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Punctal plugs have been in use for decades now to treat conditions of dry eye. More recently they have gained attention for use as drug delivery systems for the treatment of ocular diseases and conditions. Several challenges exist with formulating a drug to release at the desired daily rate and or dose that will give efficacy while limiting adverse events.

Diffusion based drug delivery systems are characterized by release rate of drug and is dependent on its diffusion through inert water insoluble membrane barrier. There are at least two types of diffusion designs, exemplary of those are reservoir devices and matrix devices. Reservoir devices are those in which a core of drug is surrounded by a polymeric membrane. The nature of the membrane determines the rate of release of drug from the system. The process of diffusion is generally described by a series of equations governed by Fick's first law of diffusion. A matrix device consists of drug dispersed homogenously throughout a polymer.

Reservoir and matrix drug delivery systems are considered diffusion based sustained release systems and constitute any dosage form that provides medication over an extended period of time. The goal of a sustained release system is to maintain therapeutic levels of drug for an extended period and this is usually accomplished by attempting to obtain zero-order release from the sustained release system. Sustained release systems generally do not attain this type of release profile but try to approximate it by releasing in a slow first order manner. Over time, the drug release rate from reservoir and matrix sustained release systems will decay and become non therapeutic.

Zero-order drug release constitutes drug release from a drug delivery system at a steady sustained drug release rate, that is, the amount of drug that is released from the drug delivery system over equal time intervals does not decay and remains at the therapeutic level. This "steady sustained release drug delivery system" is referred to as a zero-order drug delivery system and has the potential to provide actual therapeutic control by its controlled release.

Figure 1A:
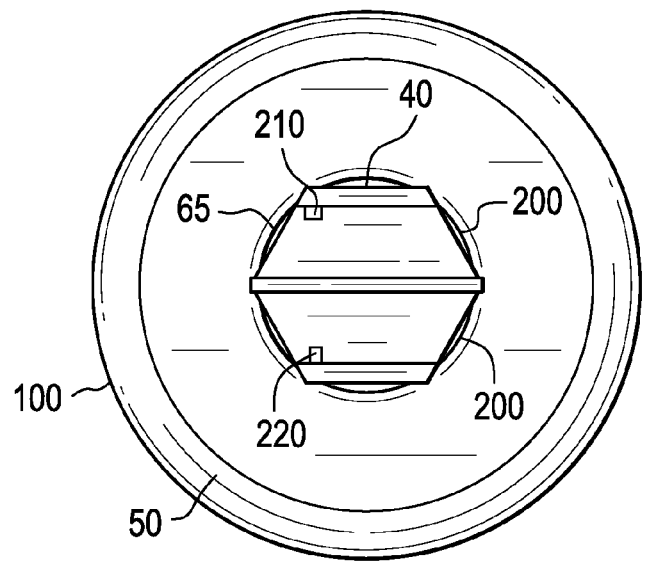
FIG. 1A illustrates an exemplary punctal plug according to the present invention with a core insert disposed within a cavity within the punctal plug.
Figure 1B:
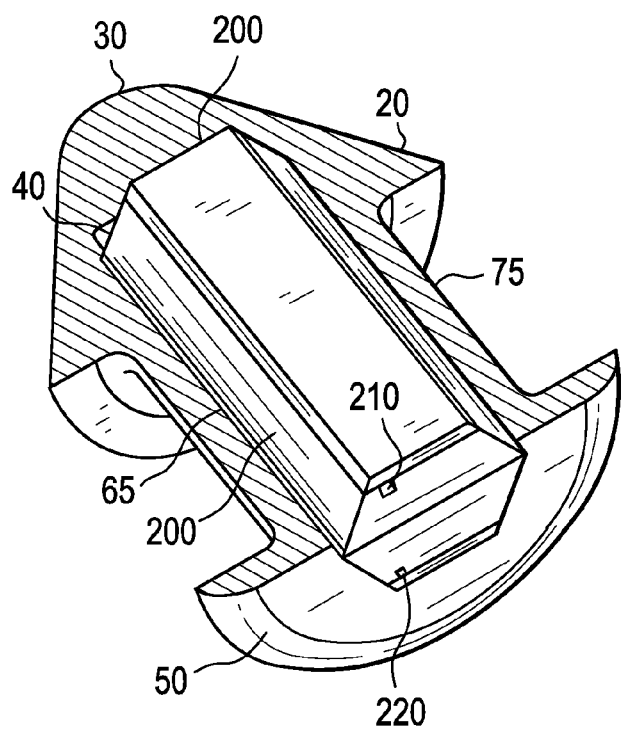
FIG. 1B illustrates a side plan view, in partial cross-section, of the illustrative punctal plug of FIG. 1.

Referring now to FIGS. 1A and 1B, there is illustrated an exemplary embodiment of a punctal plug 100 configured for pulsatile drug delivery. The punctal plug 100 may include a first end 50 having a flange or flange-like cross-sectional profile and a second end 30 having a shape or profile enabling easy insertion and good retention in the punctum. Between the first end 50 and second end 30 a drug-impermeable housing 75 may be provided. The plug 100 may include a cavity 40 defined, in part, by inner surface 65. A drug delivery core 200 is shown inserted into the cavity 40 in the punctal plug 100. The drug delivery core 200 is shown in an exemplary manner with a hexagonal shape. The drug delivery core 200 may be made with a variety of shapes or include other features to retain it within the punctal plug, also referred to herein synonymously as a lacrimal insert or simply a plug. Features, shapes, and other means of retaining a drug delivery core within a lacrimal insert are shown and described in applicants co-pending, commonly assigned U.S. patent application Ser. No. 13/043,171, which is hereby incorporated by reference in its entirety.

Figure 2:
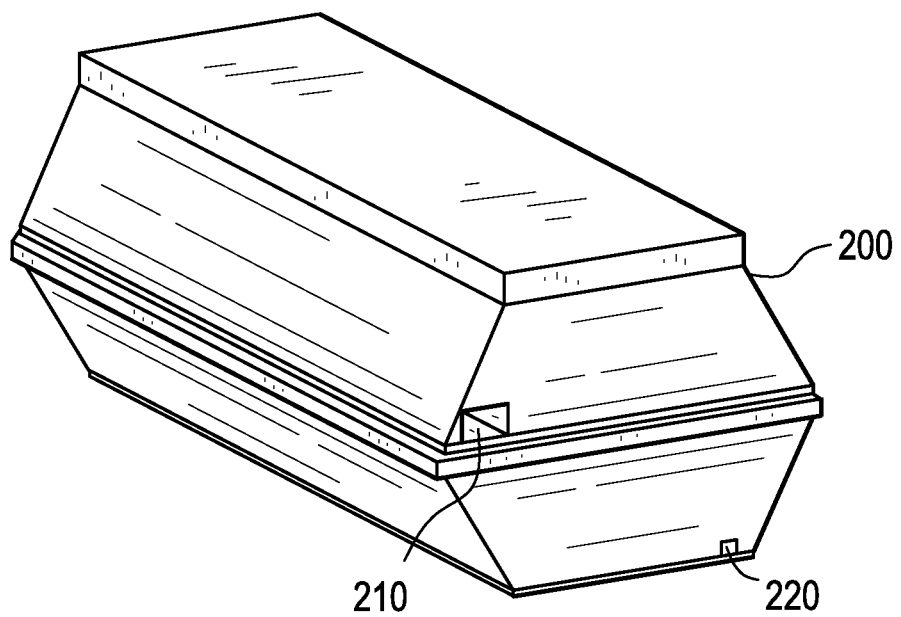
FIG. 2 illustrates an exemplary embodiment of a drug delivery core configured for insertion into a punctal plug in accordance with the present invention.
Figure 3A:
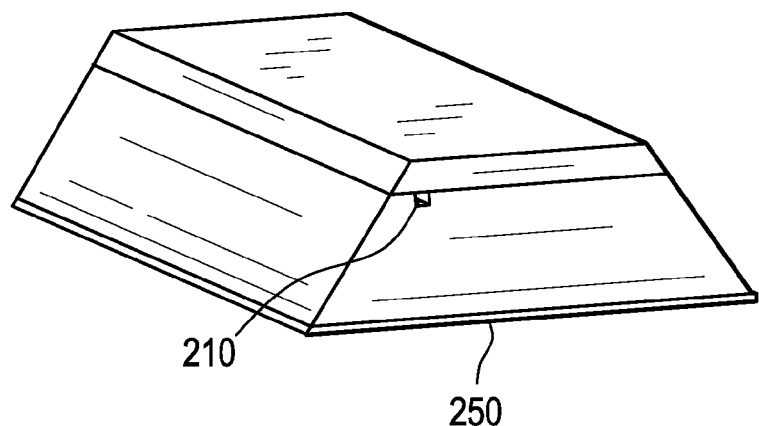
FIGS. 3A and 3B illustrate an exemplary embodiment of the drug delivery core separated into its two primary components.
Figure 3B:
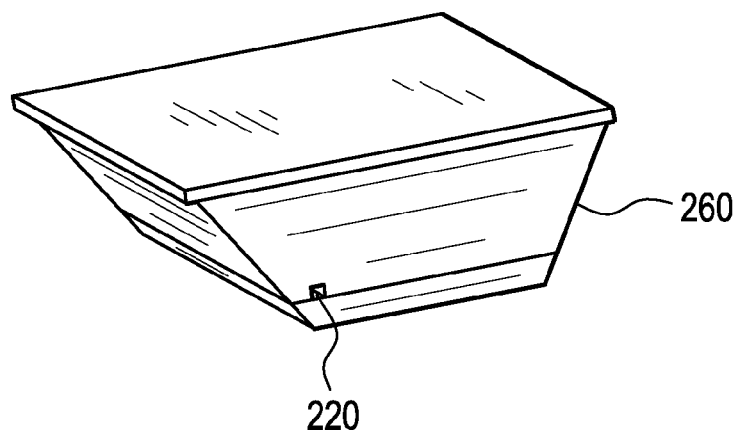

FIG. 2 illustrates the drug delivery core 200 removed from the lacrimal insert 100. The exemplary drug deliver core 200 is shown having at least one fluid inlet port 210 and one fluid outlet port 220. When used for ocular therapy, the disclosed arrangement permits lacrimal fluid to enter the drug delivery core 200 via the inlet port 210. Material within one chamber of the drug delivery core then swells or increases in volume as water and/or other material from the lacrimal fluid is absorbed by a medium in the chamber, and exerts pressure on a second opposite chamber comprising, at least in part, a therapeutic agent. The therapeutic agent may then be expelled through the outlet port 220. FIGS. 3A and 3B further illustrate an exemplary embodiment of the present invention wherein the drug delivery core 200 comprises essentially two basic parts; namely, an engine 250, FIG. 3A, for controlling the rate and amount of therapeutic agent that the drug reservoir 260, FIG. 3B, releases via the outlet port 220. As illustrated in greater detail in FIG. 5, the outlet port 220 may comprise a valve 221 to control the flow of fluid through the outlet port 220. For example, in one exemplary embodiment, the valve 21 may comprise an elastomeric check valve configured to prevent backflow into the outlet port 220.

Figure 4:
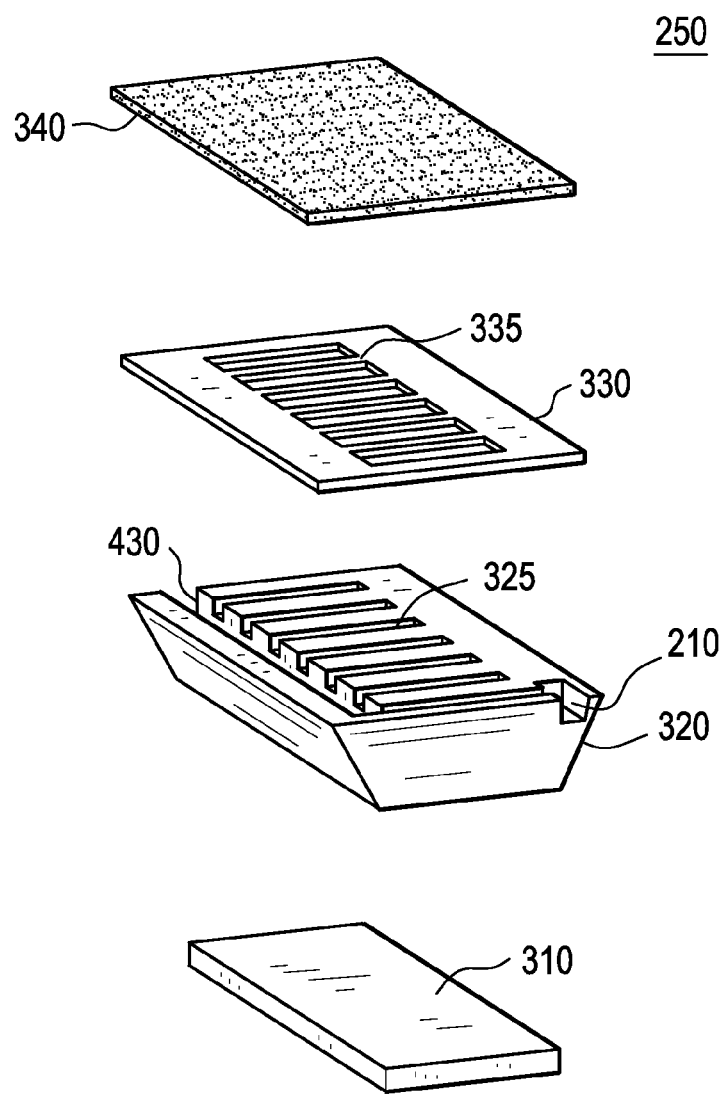
FIG. 4 illustrates an exemplary embodiment of the present invention with the portion of the drug delivery core containing a swell plate shown in exploded view.

FIG. 4 illustrates an exploded view of an exemplary embodiment of the engine 250, in exploded view. The engine 250 may include a swell chamber 320 that has a plurality of individual swell compartments 325 which are each in fluid communication with a single or multiple timer channels 430 that permits a fluid, such as water or lacrimal fluid, to enter the engine 250 via the inlet port 210 and be carried to the swell compartments 325. Although not shown in the all the figures, those of ordinary skill in the art will recognize that a check valve or restrictor may be employed at the inlet port 210 to inhibit effluence of material via the inlet port 210. This valve may be similar to valve 221 described above. A film layer 330, preferably having an adhesive applied thereto, may be included to seal a portion of the swell chamber 320. The film layer 330 may include a plurality of swell slots 335 that correspond to each swell compartment 325 built into the swell chamber 320. Further, a flexible membrane 340 and cover plate 310 may be used to fully seal the engine 250.

The timer channel 430, in a preferred exemplary embodiment, may be filled with a water soluble material that dissolves at a predictable, known rate. As the material in the timer channels 430 dissolves, fluid is able to reach each of the swell compartments 325. Once the fluid reaches a swell compartment 325, depending on the materials disposed in each swell compartment 325, not illustrated in FIG. 4, the material in each swell compartment 325 will emit gas or absorb fluid, thereby increasing in volume (swell). Typical materials that might be disposed in each swell compartment 325 may include cross linked polyacrylic acids and derivatives thereof, known as superabsorbing polymers or SAP. Alternately or in combination therewith, some or all of the swell compartments 325 may be filled with a material that will gas when exposed to fluid from the timer channel 430. Such materials may include dry mixtures of acids and carbonates or bicarbonates, such as a mixture of sodium bicarbonate and citric acid.

Figure 5:
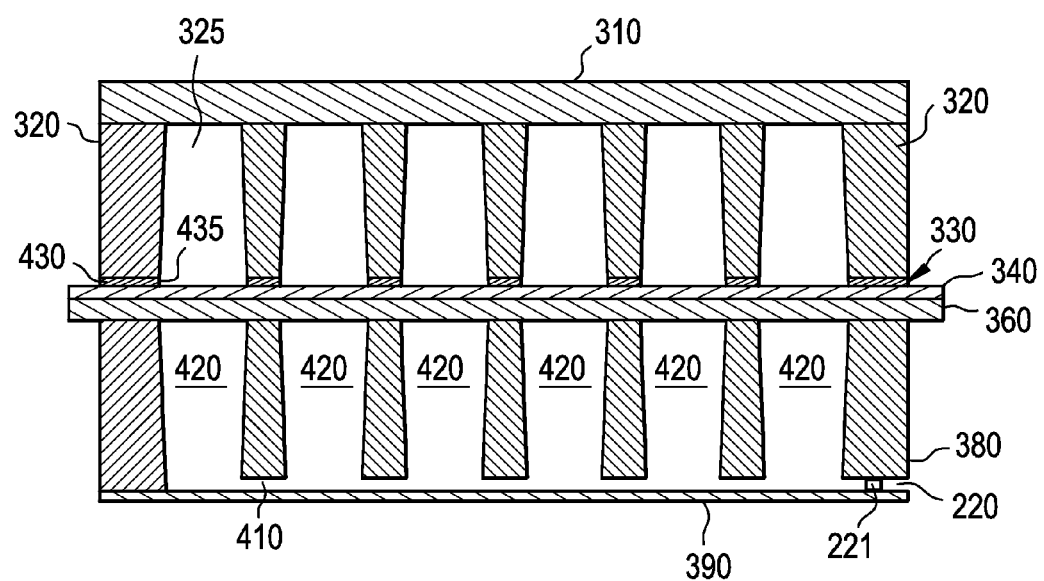
FIG. 5 illustrates an exemplary embodiment of the present invention in cross-sectional view showing a portion of the drug delivery core having a swell plate and a drug chamber.

FIG. 5 illustrates an exemplary embodiment of a drug delivery core insert 200, as illustrated in FIGS. 1A and 1B, of the present invention, in cross section and partial cutaway view. Shown is an example of how the swell chamber 320 and drug chamber 380 are integrated to permit the swell chamber 320 to act as an engine for expelling material, typically a therapeutic agent for the treatment of an ocular condition, from the drug chamber 380.

As illustrated, the drug chamber 380 may include a cover 390. In one exemplary embodiment the cover 390 may be made of polyethylene terephthalate or PET foil. The drug chamber 380 has one or more drug reservoirs 420 configured to hold or contain a quantity of therapeutic agent, which may or may not be combined with carriers, fillers, and the like. Each drug reservoir 420 is in fluid communication with a single or multiple drug channels 410 that permit the therapeutic agent to be expelled from the drug delivery core insert 200 via the fluid outlet 220.

Figure 6:
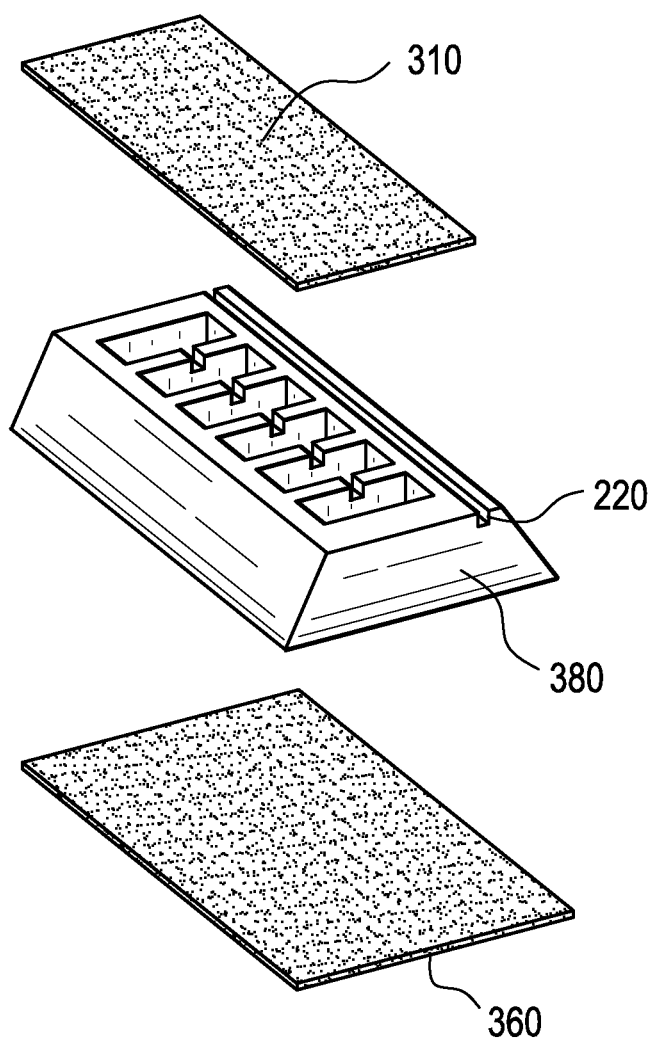
FIG. 6 illustrates an exemplary embodiment of the present invention with the portion of the drug delivery core containing a drug chamber shown in exploded view.

Between the swell chamber 320 and the drug chamber 380, there may be one or more flexible membranes 360 to maintain separation of the fluid entering the swell chamber 320 from the drug chamber 380. The flexible membrane 360 may be affixed to the drug chamber 380 via any suitable means, for example, using an adhesive, such as silicone adhesive or other adhesive that does not react with the therapeutic agent or other materials it may come in contact with. Another flexible membrane 340 may also be used to seal the swell chamber 320 with the membranes 360 and 340 joined using an adhesive, such as an acrylic adhesive. FIG. 6 illustrates an exemplary embodiment of the drug chamber 320 in exploded view.

Figure 7:
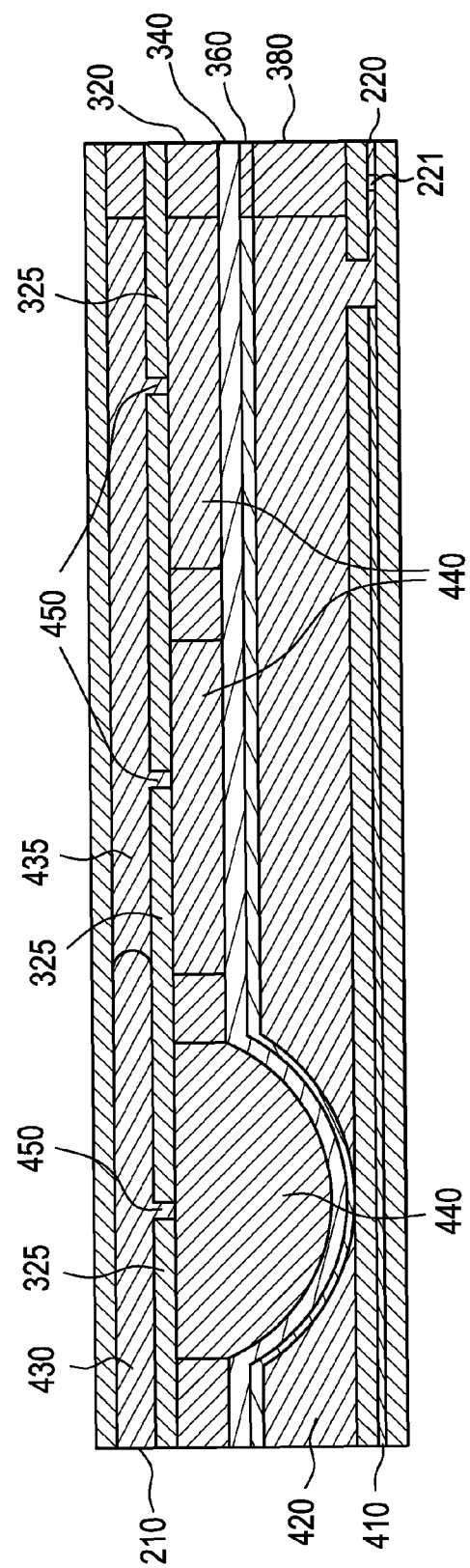
FIG. 7 is an illustrative depiction of a cross-sectional view of the drug delivery core as it might appear during use in accordance with the present invention.

FIG. 7 illustrates an exemplary embodiment of the invention in which lacrimal fluid enters the swell chamber via inlet port 210. The timer channel 430 is initially filled with a soluble, in lacrimal fluid, timer material or substance 435. Over time and at a predictable rate, the material in the timer channel 430 dissolves, permitting the lacrimal fluid to reach each swell compartment 325 via fluid ports 450. Over time and as the timer substance 435 dissolves, the lacrimal fluid may enter each swell compartment 325. The swellable material 440 in the swell compartment 325 may absorb the lacrimal fluid and begin to increase in volume. In an alternate exemplary embodiment, not shown, the swellable material 440 may be replaced with a gassing material that creates a volume increase by emitting gas when the gassing material comes in contact with the lacrimal fluid.

As the swellable material 440 increases in volume, it exerts pressure against the flexible membrane 340 which in turn expands into the space occupied by the drug reservoir 420 causing the therapeutic agent in the drug reservoir 420 to be expelled via the drug channel 410 and through the fluid outlet 220. To create a pulsatile drug delivery profile, a series of fluid ports 450 spaced along the timer channel 430 determine the approximate rate at which lacrimal fluid may enter each swell compartment 325. Each time the lacrimal fluid enters a successive fluid port 450, a pulse of therapeutic agent is emitted from the drug delivery core 200. The number of pulses that a device may emit is, therefore, determined, at least in part, by the number of swell compartments incorporated into a device. The rate at which pulses are emitted is a function of the rate that the timer material 435 dissolves and the distance between the fluid ports 450.

As used herein, the term active agent refers to an agent capable of treating, inhibiting and/or preventing a disorder or a disease. Exemplary active agents include pharmaceuticals and nutraceuticals. Preferred active agents are capable of treating, inhibiting, or preventing a disorder or a disease of one or more of the eye, nose and throat.

As used herein, the term punctal plug refers to a device of a size and shape suitable for insertion into the inferior or superior lacrimal canaliculus of the eye through, respectively, the inferior or superior lacrimal punctum. Exemplary and illustrative devices are disclosed in U.S. Pat. No. 6,196,993 and U.S. Published Patent Application No. 20090306608A1, both of which are hereby incorporated by reference in their entireties.

As used herein, the term opening refers to an opening in the body of a device of the present invention of a size and shape through which the active agent may pass. Preferably, only the active agent and formulation may pass through the opening. The opening may be covered with a valve, membrane, single or multiple pores, mesh, grid or it may be uncovered. The valve, membrane, mesh, or grid may be one or more of porous, semi-porous, permeable, semi-permeable, and biodegradable. The valve, membrane, mesh or grid may comprise any suitable biocompatible material.

The devices of the present invention have a reservoir in which is found an active agent-containing material and an active agent therein. The active agent may be dispersed throughout the active agent-containing material or dissolved within the material. Alternately, the active agent may be contained in inclusions, particulates, droplets, or micro-encapsulated within the material. Still in another alternate exemplary embodiment, the active agent may be covalently bonded to the material and released by hydrolysis, enzymatic degradation and the like. Yet in still another alternate exemplary embodiment, the active agent may be positioned or contained within a reservoir within the material.

Without being bound to any particular theory, it is believed that an active agent-containing material that does not undergo significant chemical degradation during the time desired for the release of active agent will release the agent by diffusion through the matrix to a device's release surfaces, meaning surfaces of the active agent-containing material in contact with a person's body fluid. According to Fick's Law, the diffusive transport or flux, J, of the agent through the active agent-containing material is governed at each point and each time by the local concentration gradient, the diffusivity of the active agent with the material D, and the spatial variation of the cross-sectional geometry of the device.

Suitable polymeric materials for the active agent-containing and/or therapeutic material include hydrophobic and hydrophilic absorbable and non-absorbable polymers. Generally, liquid, gel and other soluble drug formulations are preferred. Alternatively, suitable hydrophobic, non-absorbable polymers include ethylene vinyl alcohol ("EVA"), fluorinated polymers including polytetrafluoroethylene ("PTFE") and polyvinylidene fluoride ("PVDF"), polypropylene, polyethylene, polyisobutylene, nylon, polyurethanes, polyacrylates and methacrylates, polyvinyl palmitate, polyvinyl stearates, polyvinyl myristate, cyanoacrylates, epoxies, silicones, copolymers thereof with hydrophobic or hydrophilic monomers, and blends thereof with hydrophilic or hydrophobic polymers and excipients.

Hydrophilic, non-absorbable polymers useful in the present invention include cross-linked poly(ethylene glycol), poly(ethylene oxide), poly(propylene glycol), poly(vinyl alcohol), poly(hydroxyethyl acrylate or methacrylate), poly (vinylpyrrolidone), polyacrylic acid, poly(ethyloxazoline), and poly(dimethyl acrylamide), copolymers thereof with hydrophobic or hydrophilic monomers, and blends thereof with hydrophilic or hydrophobic polymers and excipients.

Hydrophobic, absorbable polymers that may be used include aliphatic polyesters, polyesters derived from fatty acids, poly(amino acids), poly(ether-esters), poly(ester amides), polyalkylene oxalates, polyamides, poly(iminocarbonates), polycarbonates, polyorthoesteres, polyoxaesters, polyamidoesters, polyoxaesters containing amine groups, phosphoesters, poly)anhydrides), polypropylene fumarates, polyphosphazenes, and blends thereof. Examples of useful hydrophilic, absorbable polymers include polysaccharides and carbohydrates including cross linked alginate, hyaluronic acid, dextran, pectin, hydroxyethyl cellulose, hydroxy propyl cellulose, gellan gum, guar gum, keratin sulfate, chondroitin sulfate, dermatan sulfate, proteins including collagen, gelatin, fibrin, albumin and ovalbumin, and phospholipids including phosphoryl choline derivatives and polysulfobetains.

In one exemplary embodiment, the active agent-containing material is a polymeric material that is polycaprolactone. In another exemplary embodiment, the active agent containing material comprises poly(epsilon-caprolactone), and ethylene vinyl acetate of molecular weights between about 10,000 and 80,0000. About 0 to about 100 weight percent polycaprolactone and about 100 to about 0 weight percent of the ethylene vinyl acetate are used based on the total weight of the polymeric material and, as well, about fifty (50) percent each of polycaprolactone and ethylene vinyl acetate is used.

The polymeric material used may be greater than about ninety-nine (99) percent pure and the active agents may be greater than about ninety-seven (97) percent pure. One of ordinary skill in the art will recognize that in compounding, the conditions under which compounding is carried out will need to take into account the characteristics of the active agent to ensure that the active agents do not become degraded by the process. The polycaprolactone and ethylene vinyl acetate preferably are combined with the desired active agent or agents, micro-compounded, and then extruded.

The present invention encompasses numerous devices for the delivery of active agents to the eye each having various features and advantages. For example, certain devices may have a body with a first end, a second end, and a lateral surface extending between the two ends. The lateral surface preferably has an outer diameter that is substantially circular in shape and, thus, the body preferably has a cylindrical shape. A portion of the lateral surface of certain of the devices preferably has an outer diameter that is greater than the outer diameter of the remainder of the lateral surface as illustrated in FIG. 1A. The enlarged portion may be any size or shape, and may be present on any part of the lateral surface. In exemplary punctal plug embodiments, the enlarged portion is of a size so that it at least partially anchors the punctal plug in the lacrimal canaliculus and preferably, the enlarged portion is at one end of the plug. One of ordinary skill in the relevant art will recognize that any of a wide variety of shapes is possible.

The body of the punctal plugs in accordance with the present invention may take any shape and size. Preferably, the body may be in the shape of an elongated cylinder. The body may be about 0.8 mm to about 5 mm in length and preferably about 1.2 mm to about 2.5 mm in length. The width of the body may be about 0.2 mm to about 3 mm and preferably 0.3 mm to about 1.5 mm. The size of the opening may be from about 1 nm to about 2.5 mm and preferably about 0.15 mm to about 0.8 mm. Instead of one large opening at any one location, multiple small openings may be used. The body of the punctal plug may be wholly or partially transparent or opaque. Optionally, the body may include a tint or pigment that makes the punctal plug easier to see when it is placed in a punctum.

The body of the devices of the present invention may be made of any suitable biocompatible material including silicone, silicone blends, silicone co-polymers, for example, hydrophilic monomers of polyhydroxyethylmethacrylate ("pHEMA"), polyethylene glycol, polyvinylpyrrolidone, and glycerol, and silicone hydrogel polymers, for example, those described in U.S. Pat. Nos. 5,962,548, 6,020,445, 6,099,852, 6,367,929, and 6,822,016, incorporated herein in their entireties by reference. Other suitable biocompatible materials include polyurethane, polymethylmethacrylate, poly(ethylene glycol), poly(ethylene oxide), poly(propylene glycol), poly(vinyl alcohol), poly(hydroxyethyl methacrylate), poly (vinylpyrrolidone) ("PVP"), polyacrylic acid, poly(ethyloxazoline), poly(dimethyl acrylamide), phospholipids, for example, phosphoryl choline derivatives, polysulfobetains, acrylic esters, polysaccharides and carbohydrates, for example, hyaluronic acid, dextran, hydroxyethyl cellulose, hydroxylpropyl cellulose, gellan gum, guar gum, heparan sulfate, chondroitin sulfate, heparin, and alginate; proteins such as, for example, gelatin, collagen, albumin, and ovalbumin; polyamino acids, fluorinated polymers, for example, PTFE, PVDF, and Teflon, polypropylene; polyethylene, nylon, and EVA.

The surface of the devices of the present invention may be wholly or partially coated. The coating may provide one or more of lubriciousness to aid insertion, muco-adhesiveness to improve tissue compatibility, and texture to aid in anchoring the device. Examples of suitable coatings include gelatin, collagen, hydroxyethyl methacrylate, PVP, PEG, heparin, chondroitin sulphate, hyaluronic acid, synthetic and natural proteins, and polysaccharides, thiomers, thiolated derivatives of polyacrylic acid and chitosan, polyacrylic acid, carboxymethyl cellulose and the like as well as combinations thereof.

Certain exemplary embodiments of the devices of the present invention have a body made of a flexible material that conforms to the shape of whatever it contacts. Optionally, in the exemplary punctal plug embodiment, there may be a collarette formed of either a less flexible material than that of the body or material that too conforms to the shape of whatever it contacts. When a punctal plug having both a flexible body and a less flexible collarette is inserted into the lacrimal canaliculus, the collarette rests on the exterior of the lacrimal punctum and the body of the punctal plug conforms to the shape of the lacrimal canaliculus. The reservoir and the body of such punctal plugs are preferably coterminous. That is, the reservoir of such punctal plugs preferably makes up the entirety of the body, except for the collarette.

In exemplary embodiments in which one or both of a flexible body and collarette are used, the flexible body and flexible collarette may be made of materials that include nylon, polyethylene terephthalate ("PET"), polybutylene terephthalate ("PBT"), polyethylene, polyurethane, silicone, PTFE, PVDF, and polyolefins. Punctal plugs made of nylon, PET, PBT, polyethylene, PVDF, or polyolefins are typically manufactured using extrusion processing, injection molding, or thermoforming. Punctal plugs made of latex, polyurethane, silicone, or PTFE are typically manufactured using solution-casting processes.

Processes for manufacturing the punctal plugs in accordance with the present invention are well known. Typically, the devices are manufactured by injection molding, cast molding, transfer molding or the like. The drug delivery core parts comprise polymer, silicon (wafer) or glass and may be manufactured by means of injection molding, compression molding, cast molding, laser processing, powder blasting, etching and other related technologies and generic material removal methods. Preferably, the reservoir is filled with one or both of at least one active agent and the active agent-containing material subsequent to the manufacture of the device. Additionally, one or more excipients may be combined with the active agent alone or in combination with the polymeric material.

The amount of active agent used in the devices of the present invention will depend upon the active agent or agents selected, the desired doses to be delivered via the device, the desired release rate, and the melting points of the active agent and active agent-containing material. Preferably, the amount of active agent used is a therapeutically effective amount meaning an amount effective to achieve the desired treatment, inhibitory, or prevention effect. Typically, amounts of about 0.05 to about 8,000 micrograms of active agents may be used. Also, typical dosage or pulse intervals might comprise from about 1 hour to about 48 hours and most preferably around 24 hours when the device is used to mimic delivery of commonly available therapeutic agents for treatment of glaucoma or dry eyes. Intervals outside of this non-exhaustive range are quite possible, depending on the nature of treatment, which may include inflammation, infection, allergy, or similar ocular ailments commonly addressed using eye drops.

In accordance with certain aspects of the present invention, the reservoir may be refilled with a material after substantially all of the active agent-containing material has dissolved or degraded and the active agent is released. For example, the new active agent-containing material may be the same as, or different from, the previous polymeric material, and may comprise at least one active agent that is the same as, or different from the previous active agent. Certain punctal plugs used for particular applications may preferably be refilled with a material while the punctal plugs remain inserted in the lacrimal canaliculus, while other punctal plugs are typically removed from the lacrimal canaliculus, a new material is added, and the punctal plugs are then reinserted into the lacrimal canaliculus.

After the device is filled with the active agent, the punctal plug is sterilized by any convenient and effective method including ethylene oxide sterilization, autoclaving, irradiation, and the like as well as combinations thereof. Preferably, sterilization is carried out through gamma radiation or through the use of ethylene oxide.

The devices described herein may be used to deliver various active agents for the one or more of the treatment, inhibition, and prevention of numerous diseases and disorders. Each device may be used to deliver at least one active agent and may be used to deliver different types of active agents. For example, the devices may be used to deliver azelastine HCl, emadastine difumerate, epinastine HCl, ketotifen fumerate, levocabastine HCl, olopatadine HCl, pheniramine maleate, and antazoline phosphate for one or more of the treatment, inhibition, and prevention of allergies. The devices may be used to deliver mast cell stabilizers, for example, cromolyn sodium, lodoxamide tromethamine, nedocromil sodium, and permirolast potassium.

The devices may be used to deliver mydriatics and cycloplegics including atropine sulfate, homatropine, scopolamine HBr, cyclopentolate HCl, tropicamide, and phenylephrine HCl. The devices may be used to deliver ophthalmic dyes including rose bengal, sissamine green, indocyanine green, fluorexon, and fluorescein.

The devices may be used to deliver corticosteroids including dexamethasone sodium phosphate, dexamethasone, fluorometholone, fluorometholone acetate, loteprednol etabonate, prednisolone acetate, prednisolone sodium phosphate, medrysone, rimexolone, and fluocinolone acetonide. The devices may be used to deliver non-steroidal anti-inflammatory agents including, without limitation, flurbiprofen sodium, suprofen, diclofenac sodium, ketorolac tromethamine, cyclosporine, rapamycin methotrexate, azathioprine, and bromocriptine.

The devices may be used to deliver anti-infective agents including tobramycin, moxifloxacin, ofloxacin, gatifloxacin, ciprofloxacin, gentamicin, sulfisoxazolone diolamine, sodium sulfacetamide, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamycin, sulfadiazine, and pyrimethamine.

The devices may be used to deliver agents for one or more of the treatment, inhibition, and prevention of glaucoma including epinephrines, for example, dipivefrin, alpha-2 adrenergic receptors, including aproclonidine and brimonidine, betablockers including betaxolol, carteolol, levobunolol, metipranolol, and timolol, direct miotics, for example, carbachol and pilocarpine, cholinesterase inhibitors, including physostigmine and echothiophate, carbonic anhydrase inhibitors, for example, acetazolamide, brinzolamide, dorzolamide, and methazolamide, prostoglandins and prostamides including latanoprost, bimatoprost, uravoprost, and unoprostone cidofovir.

The devices may be used to deliver antiviral agents, including fomivirsen sodium, foscarnet sodium, ganciclovir sodium, valganciclovir HCl, trifluridine, acyclovir, and famciclovir. The devices may be used to deliver local anesthetics, including tetracaine HCl, proparacaine HCl, proparacaine HCl and fluorescein sodium, benoxinate and fluorescein sodium, and benoxnate and fluorexon disodium. The devices may be used to deliver antifungal agents, including fluconazole, flucytosine, amphotericin B, itraconazole, and ketoconazole.

The devices may be used to deliver analgesics including acetaminophen and codeine, acetaminophen and hydrocodone, acetaminophen, ketorolac, ibuprofen, and tramadol. The devices may be used to deliver vasoconstrictors including ephedrine hydrochloride, naphazoline hydrochloride, phenylephrine hydrochloride, tetrahydrozoline hydrochloride, and oxymetazoline. Finally, the devices may be used to deliver vitamins, antioxidants, and nutraceuticals including vitamins A, D, and E, lutein, taurine, glutathione, zeaxanthin, fatty acids and the like.

The active agents delivered by the devices may be formulated to contain excipients including synthetic and natural polymers, for example, polyvinylalcohol, polyethyleneglycol, PAA (polyacrylic acid), hydroxymethyl cellulose, glycerine, hypromelos, polyvinylpyrrolidone, carbopol, propyleneglycol, hydroxypropyl guar, glucam-20, hydroxypropyl cellulose, sorbitol, dextrose, polysorbate, mannitol, dextran, modified polysaccharides and gums, phosolipids, and sulphobetains.

In another exemplary embodiment of the present invention, the punctal plug drug delivery system may produce a steady and/or sustained drug delivery release rate that is driven by a water penetration mechanism that induces an osmotically controlled mechanical displacement using an inorganic water-soluble osmogent such as magnesium sulphate, sodium chloride, sodium sulphate, potassium chloride or sodium bicarbonate, and combinations and mixtures thereof.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A lacrimal insert, comprising:
a body having a first end and a second end;
a surface extending between the two ends;
a cavity within the body; and
a drug core insert, configured for insertion into the cavity of the lacrimal insert, wherein the drug core insert comprises an engine and a drug chamber, the engine including a fluid inlet for lacrimal fluid, a timer channel filled with a water soluble material, a swell chamber including a plurality of individual one or more swell compartments that are each in fluid communication with the timer channel, the timer channel being configured to allow lacrimal fluid to reach each individual swell compartment at a predictable rate, each individual swell compartment comprising a material that at least one of increases in volume or emits a gas as the lacrimal fluid from the timer channel reaches the individual swell compartment, and a flexible membrane positioned over the swell chamber and positioned between the swell chamber and the drug chamber and covering each of the individual swell compartments, the drug chamber including a plurality of individual drug reservoirs each comprising self-contained doses of therapeutic agents, each of the individual drug reservoirs being lined up with and opposing each of the individual swell compartments, a drug channel, and a drug outlet, wherein with an increased volume or emitted gas present in one of the plurality of swell compartments, pressure is exerted on the flexible membrane to cause the flexible membrane to push therapeutic agents out of an opposing drug reservoir into the drug channel and out of the drug channel through the drug outlet.

* * * * *